United States Patent
Fukushi

[11] Patent Number: 5,315,556
[45] Date of Patent: May 24, 1994

[54] SEMICONDUCTOR MEMORY HAVING IMPROVED SENSE AMPLIFIER

[75] Inventor: Isao Fukushi, Kawasaki, Japan

[73] Assignee: Fujitsu Limited, Kawasaki, Japan

[21] Appl. No.: 946,420

[22] PCT Filed: Mar. 18, 1992

[86] PCT No.: PCT/JP92/00327
§ 371 Date: Nov. 6, 1992
§ 102(e) Date: Nov. 6, 1992

[87] PCT Pub. No.: WO92/16945
PCT Pub. Date: Oct. 1, 1992

[30] Foreign Application Priority Data

Mar. 20, 1991 [JP] Japan ................... 3-057475

[51] Int. Cl.⁵ .......................... G11C 11/413
[52] U.S. Cl. ................. 365/208; 365/189.01; 365/177
[58] Field of Search ......... 365/189.01, 230.1, 190, 365/207, 208, 222, 177

[56] References Cited

U.S. PATENT DOCUMENTS 4,078,261 3/1978 Millhollan ............... 365/189.09
4,961,170 10/1990 Maki et al. ............... 365/190
5,168,467 12/1992 Fukushi ................. 365/190 X

FOREIGN PATENT DOCUMENTS

63-231791 9/1988 Japan .
2-3177 1/1990 Japan .
2-29996 1/1990 Japan .
3-104090 5/1991 Japan .
WO89/07826 8/1989 PCT Int'l Appl. .

Primary Examiner—Joseph A. Popek
Attorney, Agent, or Firm—Staas & Halsey

[57] ABSTRACT

A semiconductor memory includes a pair of write mechanisms operated in response to a write signal so that one bit line of a pair of bit lines is brought to a low potential on the basis of the write signal; a read mechanism operated in response to a read signal so that data stored in one cell of memory cells is detected via one bit line of the pair of bit lines. A pair of bipolar transistors in the read mechanism has collectors thereof connected to a high potential power supply via a load mechanism, and the emitters thereof are connected to the pair of bit lines. Pairs of gate circuits turn ON, at the read operation time, the pair of bipolar transistors by connecting a base of one of the bipolar transistors to the high potential power supply in response to the read signal, and turn OFF, at the write operation time, one of the pair of bipolar transistors by connecting the base of that bipolar transistor to the high potential, which bipolar transistor being turned OFF is being determined on the basis of the write signal. Differential amplifiers have the inputs thereof connected to the collectors of the pair of bipolar transistors whereby a potential difference between the inputs is detected.

8 Claims, 9 Drawing Sheets

SEMICONDUCTOR MEMORY HAVING IMPROVED SENSE AMPLIFIER

BACKGROUND OF THE INVENTION

1. Field of the Invention

The present invention pertains to a semiconductor memory and more particularly to an improvement of a sense amplifier in a static RAM comprised of Bi-CMOS circuits within a semiconductor memory.

In a static RAM comprised of Bi-CMOS circuits, where a bipolar transistor and p-channel and n-channel MOS transistors are present in the same chip, steps are taken to minimize an oscillation of a potential level of a common data line, which oscillation is required to enable both the reading and writing operations, so that a shift between H level and L level that takes place in both directions on the common data line can be made faster.

2. Description of the Related Art

Figure 1:
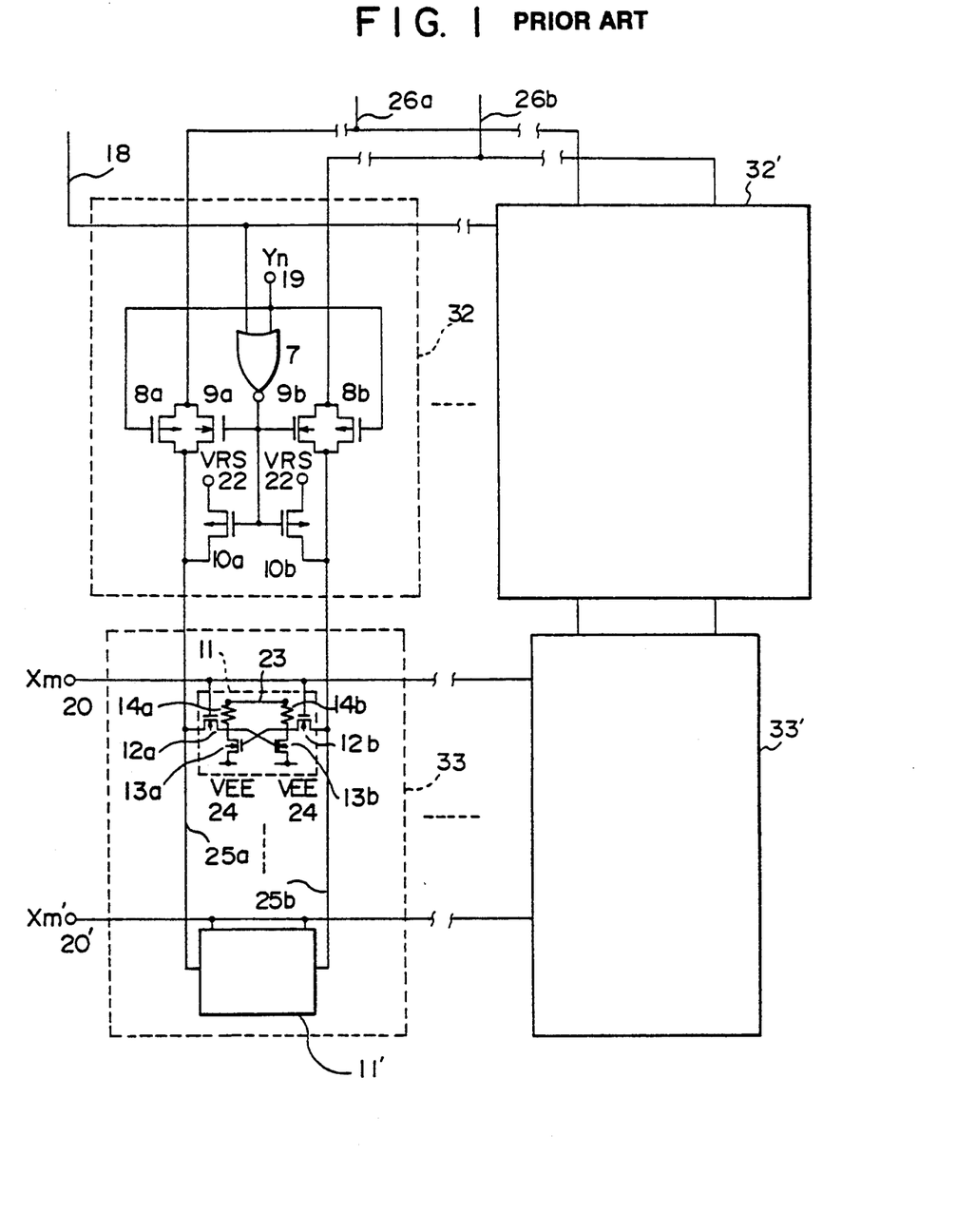
FIG. 1 is a circuit diagram of a memory cell and a bit selecting means portion in a conventional static RAM.
Figure 2:
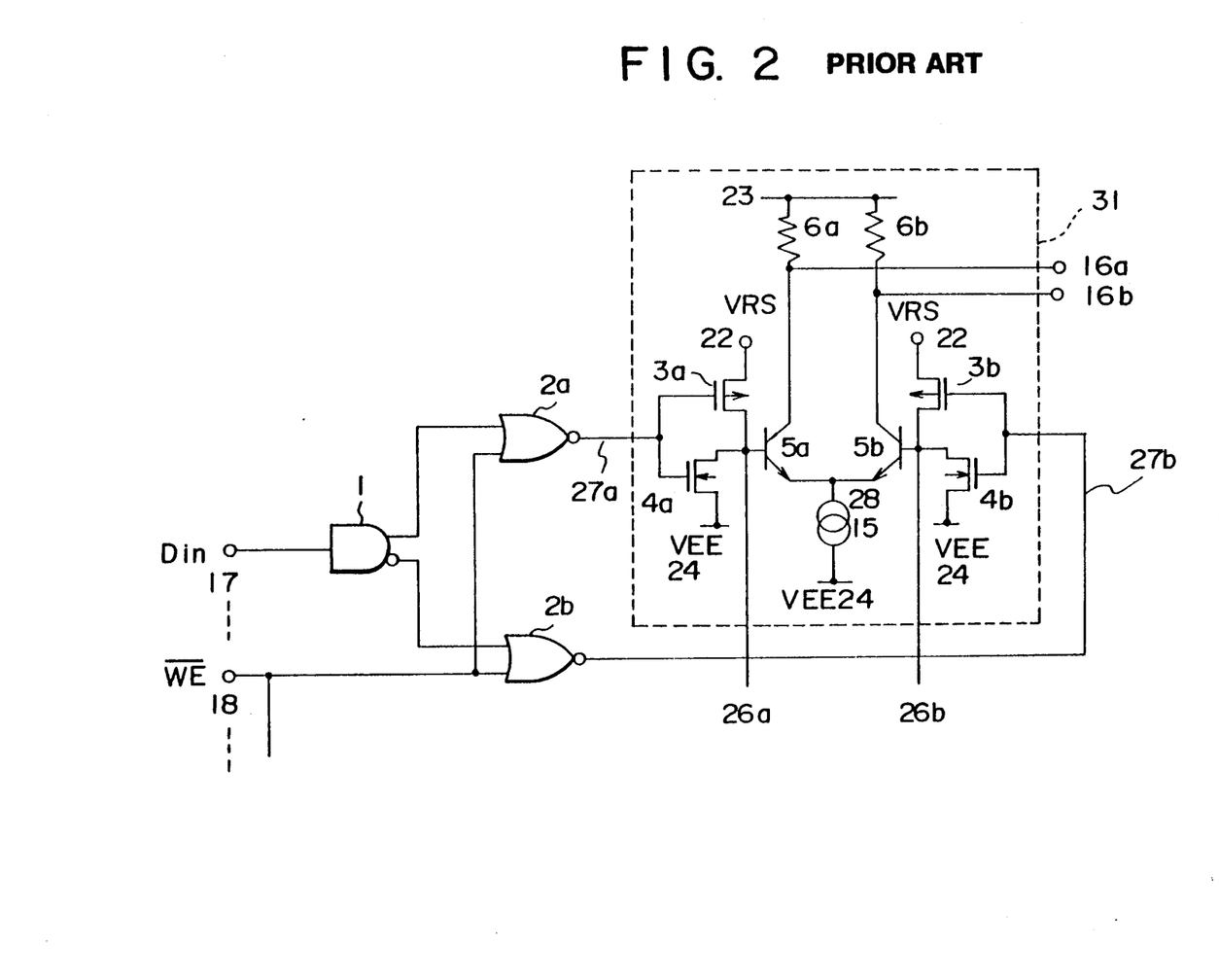
FIG. 2 is a circuit diagram of a conventional sense amplifier and an I/O portion thereof in the conventional static RAM.

A description will now be given of a static RAM comprised of conventional Bi-CMOS circuits, with reference to FIGS. 1 and 2. FIG. 1 is a circuit diagram of a memory cell and a bit selecting means portion in a conventional static RAM. FIG. 2 is a circuit diagram of a conventional sense amplifier and an I/O portion thereof in a conventional static RAM. Referring to FIG. 1, this static RAM comprises a number of memory cells 11, 11' disposed in respective columns 33 and 33' and in respective rows. The memory cells 11 and 11' in the columns 33 and 33' are supplied with respective signal lines Xm and Xm' from respective word lines 20 and 20' in each row. When the signal lines Xm and Xm' are at a logical level "H", either of the memory cells 11 or 11' becomes connected to a pair of bit lines 25a and 25b disposed in each column.

Bit selecting means 32 and 32' are disposed in correspondence with each pair of bit lines 25a and 25b, and comprise a column switch consisting of two pairs of transistors; namely a pair of n-channel MOS transistors 8a, 9a and a pair of p-channel MOS transistors 8b, 9b, and further comprising bit line load transistors 10a and 10b consisting of p-channel MOS transistors. Each of the column switches 8a and 8b begins conducting in response to the logical level "L" of a column address Yn, and connects the corresponding pair of bit lines 25a and 25b to a pair of common data lines 26a and 26b. Also, the bit load transistors 10a and 10b begin conducting so as to connect the pair of bit lines 25a and 25b to a constant-voltage regulated power supply VRS (−0.8 V, for example) 22. After the column switches 8a and 8b begin conducting, the common data lines 26a and 26b connect one of the memory cells 11 or 11' selected in accordance with a column address and a row address to a sense amplifier.

Referring to FIG. 2, a sense amplifier 31 comprises: a differential amplifier constituting an ECL circuit, which amplifier allows the signals on the common data line 26a and 26b to be received at the bases of bipolar transistors 5a and 5b and outputs the amplified results as outputs 16a and 16b of the sense amplifier 31; a pair of write n-channel MOS transistors 4a and 4b constituting a write means for receiving an input of a signal consisting of a write signal and a write data, and connecting either of the common data lines 26a and 26b to a VEE power supply (−4.5 V, for example) 24 on the basis of the write data; data line load transistors 3a and 3b consisting of a pair of p-channel MOS transistors, which transistors conduct when the write transistors 4a and 4b are OFF, thus allowing connection between the VRS power supply 22 and each of the common data lines 26a and 26b, and supplying a read current to a memory cell at the read operation time.

Gates are disposed in the input portion of the sense amplifier 31; namely a pair of NOR gates 2a and 2b which receive an input of a write signal WE' (hereinafter WE' represents a WE having a top bar) at one of the terminals thereof, and a data input gate 1 which, upon receipt of a write data Din, feeds this write data and an inverted signal on the basis of the write data to the other terminal of the above-mentioned NOR gates 2a and 2b, respectively. The outputs from each of the NOR gates 2a and 2b are fed to the inputs of the gates of the write transistors 4a and 4b, and the gates of the data line load transistors 3a and 3b.

In the above static RAM, the write signal WE' is at an "H" level at the read operation time, prompting the output from the pair of NOR gates 2a and 2b constituting the input portion of the sense amplifier to be at a level "L", and turning each of the data line load transistors 3a and 3b on. In addition, a memory cell selected at the read operation time on the basis of a row address and a column address is connected to the pair of common data lines 26a and 26b. This description, which is given in accordance with FIG. 1 assumes that the memory cell 11 of the column 33 is the selected memory cell and that a driver MOS transistor 13a therein is ON in correspondence with the data stored in the memory cell 11.

The current from the data line load transistor 3a flows into the bit line 25a via the common data line 26a, and thus reaches the VEE power supply 24 via the driver MOS transistor 13a of the memory cell 11. As a result, due to a voltage drop in the data line load transistor 3a, the potential of this common data line 26a drops significantly. However, the other common data line 26b has the same potential as the power supply VRS 22 because there is no voltage drop in the data line load transistor 3b as the driver MOS transistor 13b is off. The differential amplifier consisting of the bipolar transistors 5a and 5b, load resistors 6a and 6b, and a constant-current regulated power supply 15 detects and amplifies the potential difference between these common data lines 26a and 26b, and outputs the result as the outputs 16a and 16b of the sense amplifier 31.

At the write operation time, the write signal WE' is brought to an L level. One of outputs 27a and 27b from, respectively, the NOR gates 2a and 2b is brought to an H level and the other output to an L level, on the basis of the write data Din. Assuming that this write data Din is at a logical "L" level, the output 27a will be at an H level and the output 27b will be at an L level; the data line load transistor 3a will be OFF and the data line load transistor 3b will be ON; and the write transistor 4a will be ON and the write transistor 4b will be off. As a result of the write signal WE' being at the L level, the n-channel MOS write column switches 9a and 9b, which constitute the column switch of the bit selecting means 32, will be ON and the bit line load transistors 10a and 10b will be off. The other column switch, namely the p-channel MOS transistor 8a, will be ON in response to the row address being at an L level.

As a result of the above, a write current flows into the VEE power supply 24 via a VCC power supply (0 V, for example) 23 of the memory cell, a memory cell load resistor 14a, a transfer MOS transistor 12a, the n-channel transistor 9a and the p-channel transistor 8a, which transistors constitute column switches, the common data line 26a, and the write transistor 4a. Further, the potential of the bit line 25a is lowered to be equal to that of the VEE power supply 24, which is approximately −4.5 V, for example. On the other hand, since the other write transistor 4b is OFF, the potential of the bit line 25b is approximately equal to that of the VRS power supply 22, for example, −0.8 V. The respective potentials of the bit lines 25a and 25b force the driver MOS transistor 13b of the memory cell 11 to be OFF, prompt the other driver MOS transistor 13a to be ON, and complete the write operation of Din. When the write data Din is at "H", the write operation is carried out in the same way as described above except that the respective bit lines potentials of the bit lines 25a and 25b force the driver MOS transistor 13a (not 13b) of the memory cell 11 to be OFF and prompt the other driver MOS transistor 13b (not 13a) to be ON.

In each column not selected on the basis of a column address, the n-channel and p-channel MOS transistors 8a, 9a, 8b, and 9b, which embody column switching means, are all OFF, wherein the bit lines relevant thereto are disconnected from the common data lines 26a and 26b, and the bit line load transistors 10a and 10b retain, by being turned ON, the data of the memory cell selected on the basis of the row address.

In the conventional static RAM described above, the bases of the bipolar transistors 5a and 5b constituting a differential amplifier of the sense amplifier have different potentials; that is, the base of one transistor is at approximately the same potential level as the VRS power supply 22, while the base of the other transistor is at a potential level lowered to be approximately equal to that of the VEE power supply 24. This difference in potentials leads to a problem in that a reverse voltage is applied across the emitter and base of the above other transistor. It is normally recommended that the E-B reverse withstand voltage of a transistor in an integrated circuit be maintained to be below 5 V. The more minute a mask pattern, the lower this voltage should be. It is known, for example, that, in an extremely minute mask pattern, this E-B reverse withstand voltage is approximately 2-3 V. A serious disadvantage of the conventional static RAM is that the above-mentioned reverse voltage exceeds the E-B reverse withstand voltage.

The magnitude of the E-B reverse voltage applied to the transistors of the above ECL circuit is represented by [VEE]−[VRS]−[$V_{BE}$] (where the parenthesis [] as in [VEE] signifies an absolute value). Taking into account that a forward base-emitter voltage drop $V_{BE}$ of a transistor is normally around 0.8 V, and assuming that the voltage value of each power supply has the value specified as examples in the forgoing discussion (VEE=−4.5 V, VRS=0.8 V), the reverse voltage across the emitter and base is 2.9 V. This value means that a problem may be expected in which the emitter-base reverse voltage could exceed an E-B reverse withstand voltage $BV_{EB}$ of a transistor in an integrated circuit having a minute mask pattern, and that transistors therein are liable to degradation in characteristics or permanent breakdown due to withstand breakdown. It is known that even when the emitter-base reverse voltage does not exceed the E-B reverse withstand voltage $BV_{EB}$, some types of transistors, such as a polysilicon-base self-align transistor, are liable to degradation in characteristics, including a drop in a current gain $h_{fe}$, due to a relatively large E-B reverse voltage. Accordingly, when using such a transistor, the emitter-base reverse voltage should not only be kept below the E-B reverse withstand voltage but also be kept as low as possible.

A static RAM comprised of Bi-CMOS circuits has a disadvantage in that the lower limits of the potential oscillation of the bit lines 25a and 25b and the common data lines 26a and 26b, are determined by the lowest detectable level of the sense amplifier. These lower limits of the potential oscillation are each approximately 50 mV, for example. Maintaining the potential oscillation at a low level irrespective of the lowest detectable level of the sense amplifier allows a speedy bilateral shift to each designated potential level of the common data lines and the bit lines, which lines have large incidental capacitance, so that a speed-up of a static RAM is achieved. Though this fact is known, the conventional static RAM has the above-mentioned limitation and therefore a speed-up thereof is to a certain extent limited.

Further, although a reduction of potential oscillation is actually achieved at the read operation time as described before, the potential level of the bit line 25a is lowered to the potential level of the VEE power supply, at the write operation time. It thus takes time to return from this potential level to the original potential level that is maintained at the read operation time, which return is realized by means of the data line load transistor 3a and the bit line transistor 10a. Failure to return to the original potential level before the next read cycle can affect an access time. In addition, a speed-up of a static RAM is thwarted.

SUMMARY OF THE INVENTION

Accordingly, an overall object of the present invention is to provide a novel and useful semiconductor memory capable of eliminating the disadvantages of the above-mentioned conventional technology.

In view of the disadvantages of the above-mentioned static RAM consisting of Bi-CMOS circuits, an object of the present invention is to provide a semiconductor memory in the form of a static RAM consisting of Bi-CMOS circuits in which memory a sense amplifier portion is improved, so that no reverse voltage is applied across the emitter and base of a transistor of a differential amplifier, thereby preventing degradation of characteristics of the transistor or a breakdown thereof, the potential oscillations of the data lines and the bit lines, which lines have large incidental capacitance, can be maintained at a low level irrespective of the lowest detectable level of the sense amplifier, and a speed-up of the potential level shift of the data lines and the bit lines is achieved following the write operation and preceding the shifting to the next read cycle.

The above object of the present invention can be achieved by a semiconductor memory having a sense amplifier comprising:

a plurality of memory cells disposed in columns and rows;

a pair of bit lines disposed in each column of the memory cells and connected to the memory cells selected on the basis of a row address;

bit selecting means selected on the basis of a column address and disposed in correspondence with each of the pairs of bit lines;

a pair of common data lines disposed so as to be connected to each of the pairs of bit lines;

a pair of write means operated in response to a write signal or a write data so that one write means of the pair of write means begins conducting in response to the write data to connect one data line of the pair of common data lines to a first power supply, which is a low potential power supply;

read means operated in response to a read signal so that a data stored in one of the memory cells is detected via each of the pairs of common data lines, characterized in that the read means comprises:

a pair of bipolar transistors wherein the collectors thereof are connected, via load means, to a second power supply, which is a high potential power supply, and the emitters thereof are connected to each of the pairs of common data lines;

pairs of gate circuits which turn ON, in response to the read signal, the pair of bipolar transistors by connecting a base of one of the transistors to the second power supply, and turn OFF, on the basis of the write signal and write data, the pair of bipolar transistors by connecting the base of the other one of the bipolar transistors to the first power supply;

differential amplifiers whose inputs are connected to the collectors of the pair of bipolar transistors, wherein a potential difference between the inputs is detected.

The semiconductor memory of the present invention preferably comprises high-resistance resistors for connecting the emitters of the pair of bipolar transistors to the first power supply.

DETAILED DESCRIPTION OF THE PREFERRED EMBODIMENTS

Figure 3:
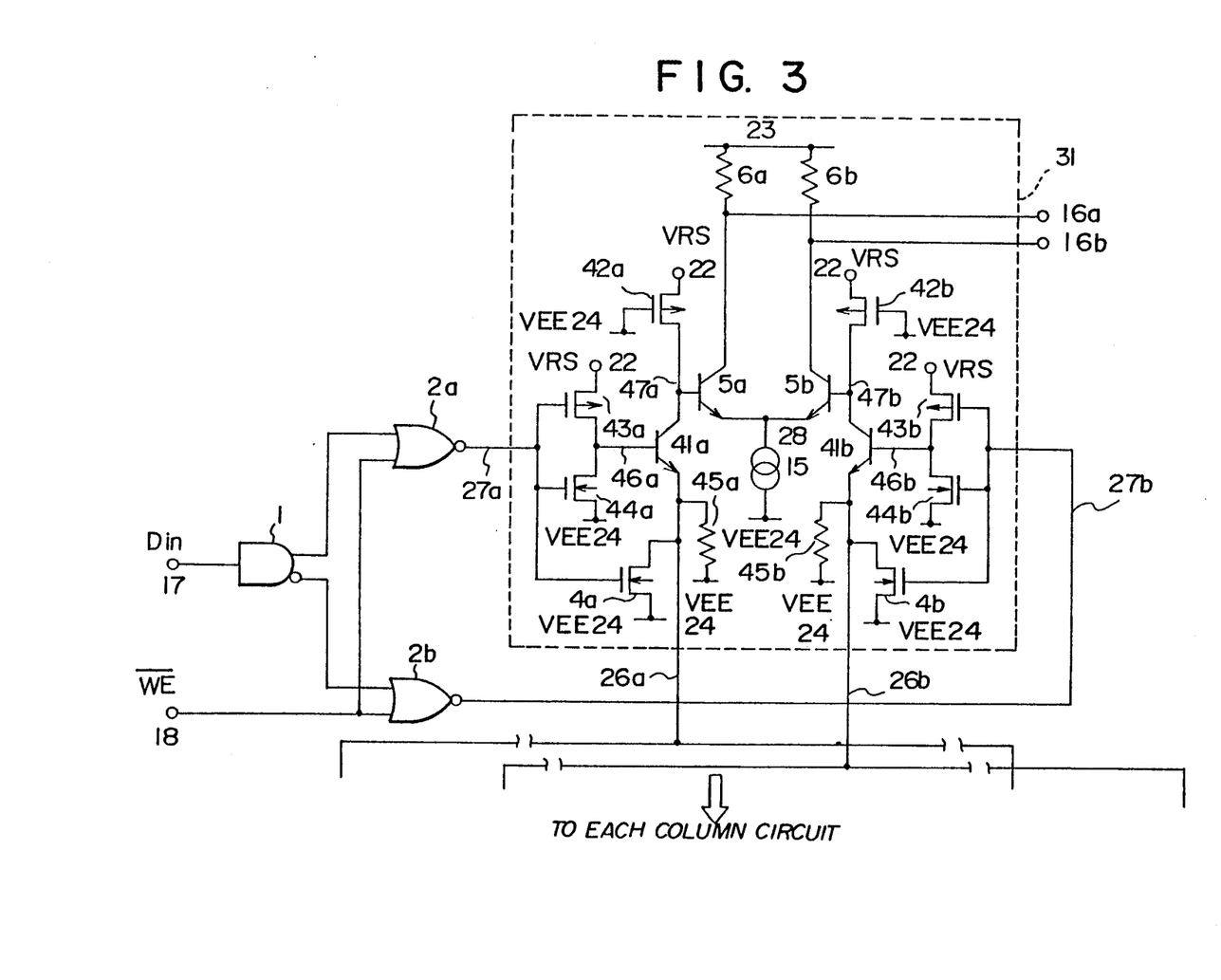
FIG. 3 is a circuit diagram of a sense amplifier and an I/O portion thereof of the first embodiment of the present invention.
Figure 4:
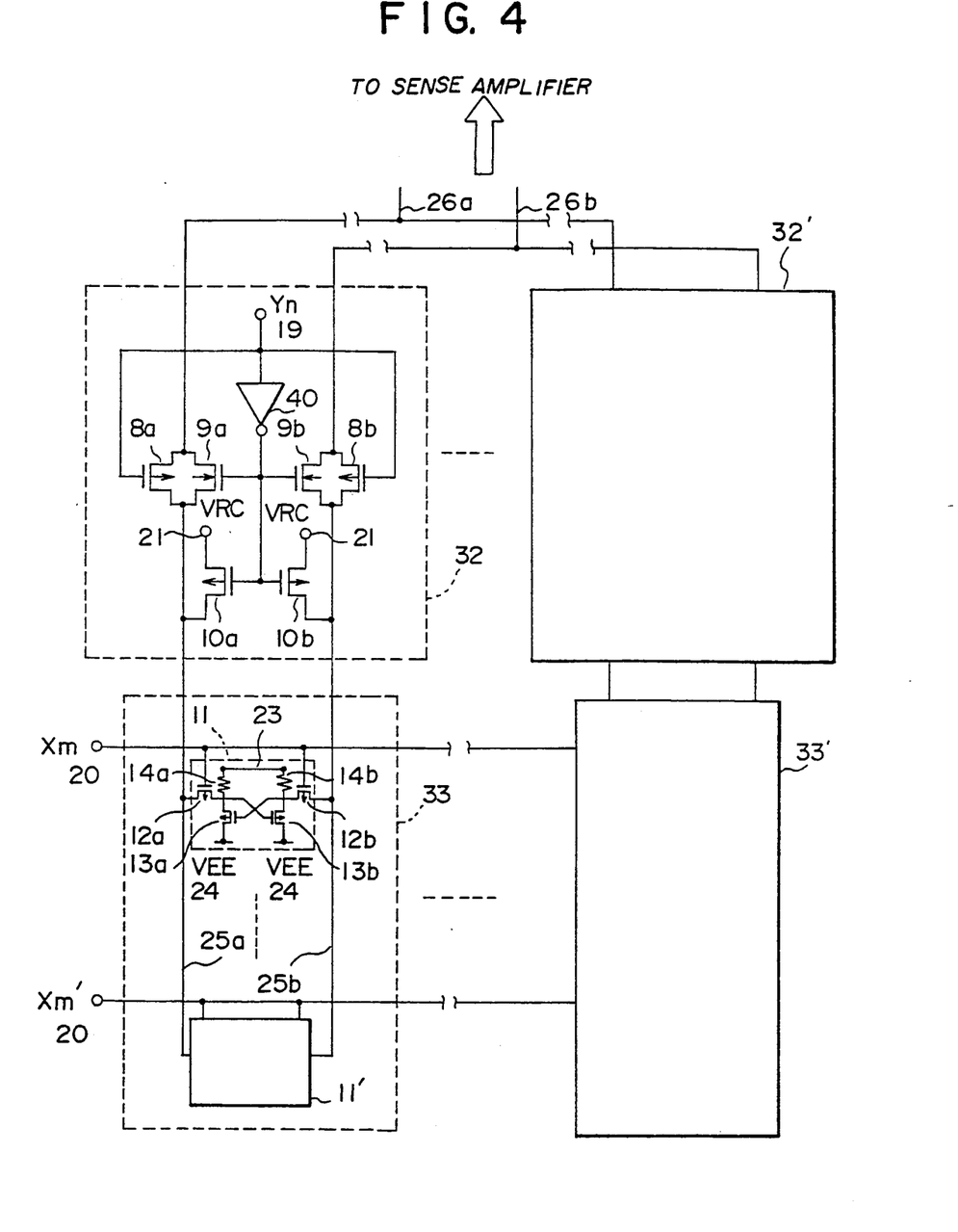
FIG. 4 is a circuit diagram of a memory cell portion and a bit selecting means portion of the first embodiment.

A detailed description will be given below of the features of the present invention that are different from the conventional semiconductor memory, in accordance with the circuit diagrams in FIGS. 3 and 4 showing an embodiment of the present invention. FIG. 3 is a circuit diagram of a sense amplifier corresponding to the conventional sense amplifier shown in FIG. 2. Similarly, FIG. 4 is a circuit diagram corresponding to FIG. 1.

A sense amplifier 31 in FIG. 3 differs from the conventional sense amplifier in that, in the stages subsequent to the NOR gates 2a and 2b, inverter gates 43a, 44a and 43b, 44b are disposed, in that a pair of bipolar transistors 41a and 41b are provided, the collectors thereof being connected, respectively, to the bases of the pair of bipolar transistors 5a and 5b constituting a differential amplifier, the emitters thereof being connected to the data lines 26a and 26b, respectively, and the bases thereof receiving the outputs from the inverter gates 43a, 44a, and 43b, 44b, in that p-channel MOS transistors 42a and 42b constituting load means are provided between the collectors of the above bipolar transistors 41a, 41b and the power supply (VRS power supply) 22, the gates of the MOS transistors being connected to a low-potential power supply (VEE power supply) 24, constituting a load means, and in that the emitters of the pair of bipolar transistors 41a and 41b are connected to the VEE power supply 24 via resistors 45a and 45b.

The bit selecting means 32 shown in FIG. 4 differs from the one shown in FIG. 1 in that an inverter 40 is provided in place of the NOR gate 7, and in that a VRC power supply (VRC=VRS−$V_{BE}$) 21 is provided separately so as to supply power to the source of the bit line load transistors 10a and 10b of the bit selecting means 32. Other configurations in FIG. 4 remain the same as those in FIG. 1. The transistors 10a and 10b are OFF when a selection is made for write and read operations and ON when a selection is not made.

At the read operation time, the write signal WE' becomes "H", the write transistors (n-channel MOS transistors) 4a and 4b become OFF, and the outputs from the inverters 46a and 46b are both "H", the potential provided opposite to the MOS transistor 13a is already OFF, so only a minute amount of current flows in the load transistor 42b to the high-resistance resistor 45b. Therefore, the potential of the base (the node 47b) of the other bipolar transistor 5b, which base is connected to the drain of the transistor 42b, is approximately the same as the potential of the VRS power supply. Accordingly, the differential amplifier consisting of the pair of bipolar transistors 5a and 5b, the load resistors 6a and 6b, and the constant-current regulated power supply, detects and amplifies the potential difference between the inputs and 47b, and then outputs the amplified result as the outputs 16a and 16b of the sense amplifier 31.

The base potential oscillation of the bipolar transistors 5a and 5b constituting the differential amplifier can be set irrespective of the potential oscillations of the common data lines 26a, 26b and the bit lines 25a and 25b, wherein, ideally, the oscillation of the common data lines, etc. is controlled to be zero. Prevention of a malfunction in detection of the potential difference by the differential amplifier, and speed-up of an operation are achieved by controlling the oscillations of the bit lines 25a, 25b and the common data lines 26a and 26b, which bit lines and data lines have great incidental capacitance, while setting the input oscillation level of the differential amplifier at a high level.

At the write operation time, the write signal WE' is brought to an "L" level. One of the outputs 27a and 27b from the NOR gates is brought to an H level and the other one to an "L" level, on the basis of the write data Din. Assuming that this write data Din is at an "L" level, the NOR gate output 27a will be at an "H" level and the NOR gate output 27b will be at an "L" level, the outputs from the inverters 43a and 44a will be at an "L" level, the outputs from the inverters 43b and 44b will be at an "H" level, and the write n-channel MOS transistors 4a and 4b will be ON and OFF respectively. The write current flows through the load resistance 14a of the memory cell 11, the transfer MOS transistor 12a, the bit line 25a, the common data line 26a, and the write n-channel MOS transistor 4a. The potential of the bit line 25a is lowered almost to the potential level of the VEE power supply 24.

Since the write transistor 4b is OFF and the transistor 41b is ON, the potentials of the bit line 25b and the common data line 26b are maintained at a level lower than the potential VRS of the VRS power supply by the emitter-base voltage $V_{BE}$ of the transistor 41b, thus forcing the driver MOS transistor 13b of the memory cell 11 to be OFF. The write operation is completed when 13a is turned ON. Since, as mentioned earlier, the transistor 41a is OFF at this time, the potential level of the collector thereof is maintained at approximately the potential level of VRS by the data line load transistor 42a, thus preventing a reverse voltage from being applied across the emitter and base of the bipolar transistor 5a constituting a part of the differential amplifier.

At the read operation time following a write operation, the write signal WE' is at "H", the write n-channel transistor 4a if OFF, the transistor 41a is turned ON, and the potentials of the bit line 25a and the common data line 26a that were lowered, at the write operation time, to the level of the potential of the VEE power supply are each returned to the original read potential level by the transistor 41a.

When the write data Din is at "H", the write operation is carried out in the same way as above described except that the suffixes a and b are reversed in sequence.

As described in Japanese Laid-Open Patent Application No. 3-104090 which the present applicant filed on Sep. 18, 1989, it is possible to prevent a reverse voltage from being applied, at the write operation time, across the emitters and bases of the bipolar transistors constituting the differential amplifier, by inserting MOS transistors between the bases of the bipolar transistors constituting the differential amplifier and the common data lines, and by turning one of these MOS transistors OFF at the write operation time.

While, in the above-mentioned circuit, the base potentials of the bipolar transistors constituting the differential amplifier are approximately the same, at the read operation time, as the potential of the common data line, thus allowing the difference between the potentials of common data lines to be read by the differential amplifier, the present embodiment provides a potential separation, at the read operation time, between the bases of the bipolar transistors 5a and 5b constituting the differential amplifier and the common data lines 26a and 26b by means of the bipolar transistors 41a and 41b, so that the bit lines 25a and 25b and the common data lines 26a and 26b, which bit lines and data lines have a large incidental capacitance, are at approximately the same potential, enabling speed-up of a read operation.

Further, the potentials of the bit lines 25a and 25b, and those of the common data lines 26a and 26b which were lowered, at the read operation time, immediately following a write operation, to the potential level of the VEE power supply, are raised to the original read potential level by the bipolar transistors 41a or 41b having a large current-driving capability, thus assuring a high-speed operation.

Figure 5:
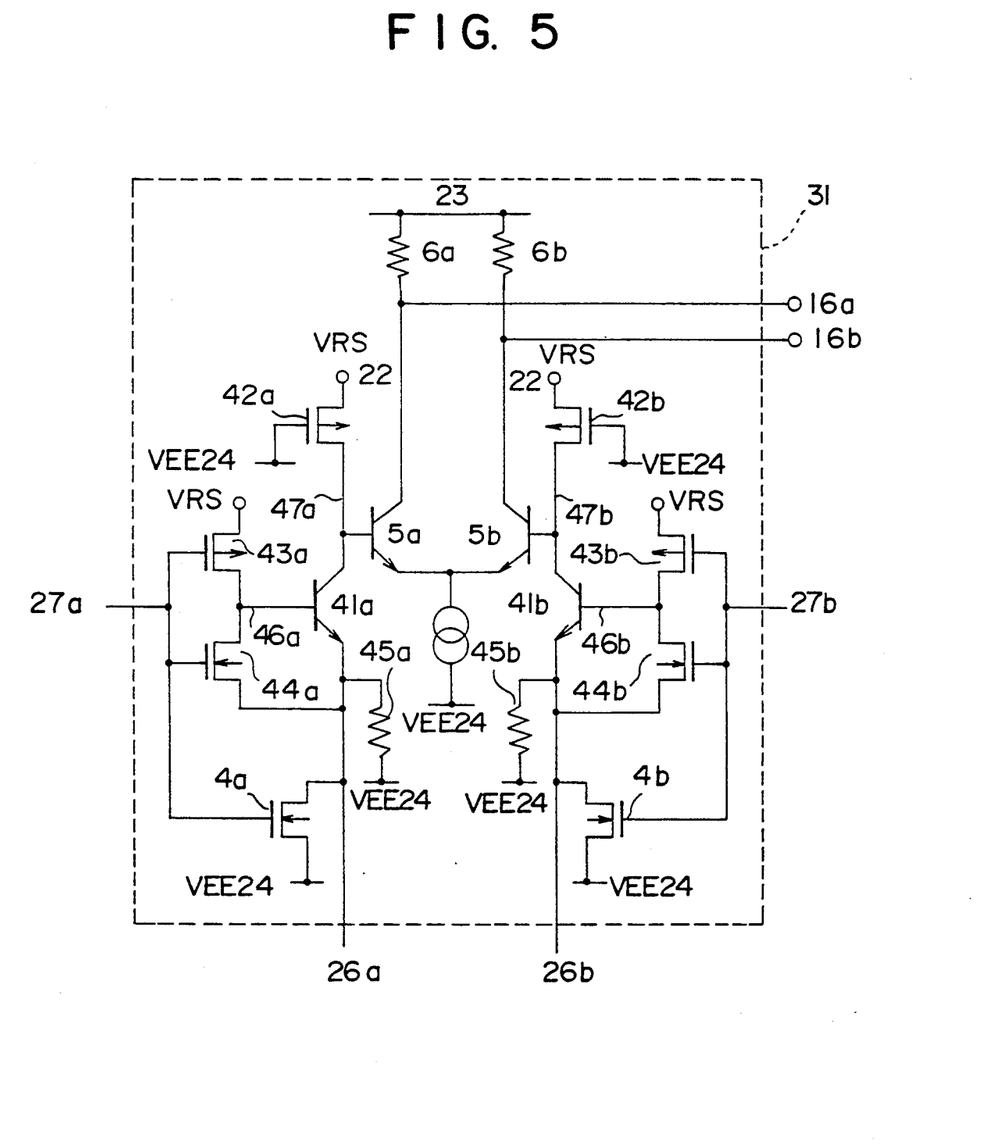
FIG. 5 is a circuit diagram of a main part of the second embodiment.

FIG. 5 is a circuit diagram of the main part of the second embodiment of the present invention. The sense amplifier of this embodiment differs from the sense amplifier of FIG. 1 in that, in the sense amplifier of this embodiment, the sources of the n-channel transistors 44a and 44b, which transistors constitute C-MOS inverters, are connected to the emitters of the transistors 41a and 41b, while in the conventional sense amplifier, this is not the case. While a problem arises regarding the configuration in FIG. 1, when the n-channel MOS transistors 44a and 44b are turned ON so that the transistors 41a and 41b are OFF when the inverters are operated, in that the potential level of the bases of the transistors 41a and 41b drop to the potential level of VEE faster than does the potential level of the emitters, with the result that a reverse voltage could be applied across the emitters and bases of the transistors 41a and 41b, the configuration of FIG. 5 ensures that the possibility of reverse voltage is eliminated because the bases and emitters of the transistors 41a and 41b are at the same potential due to the conducting state of the MOS transistors 44a and 44b.

Figure 6:
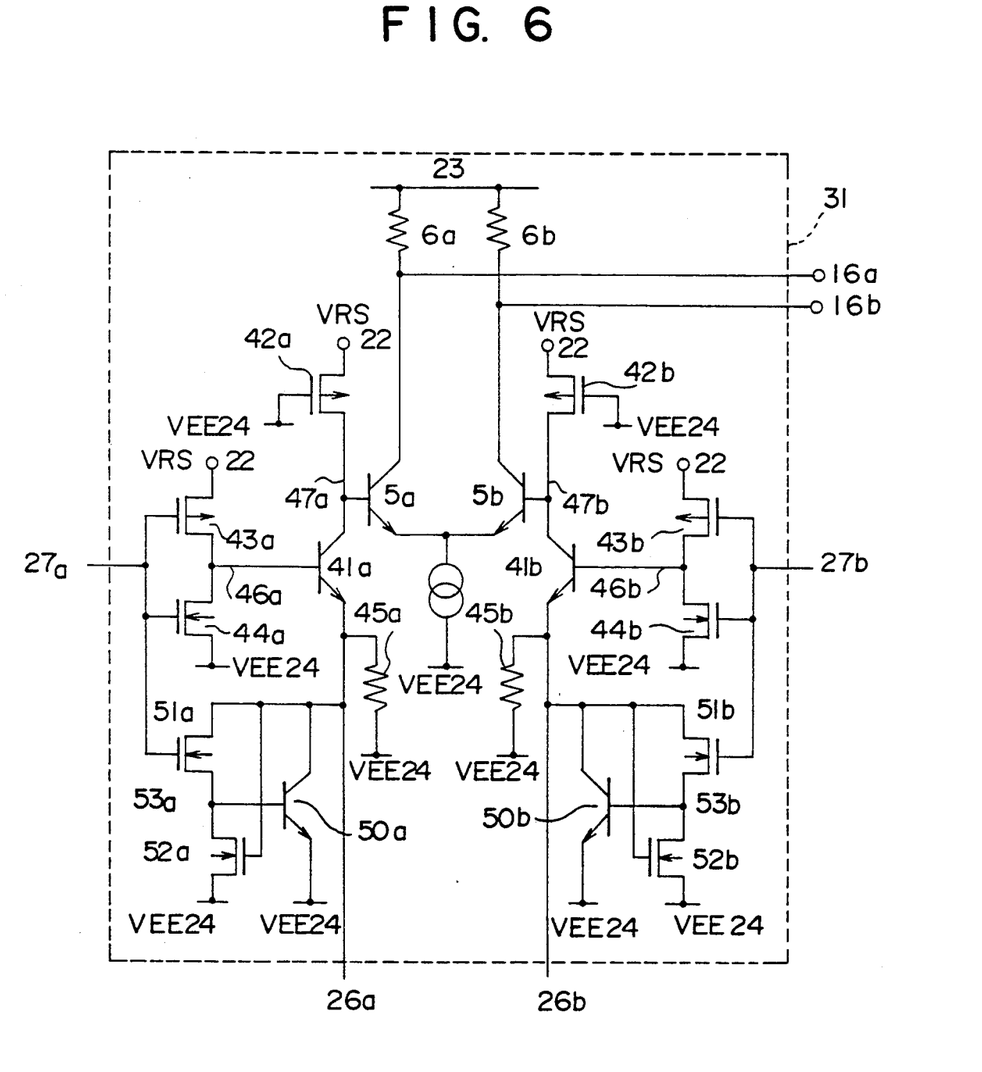
FIG. 6 is a circuit diagram of a main part of the third embodiment.

FIG. 6 is a circuit diagram of the main part of the third embodiment of the present invention. The sense amplifier of this embodiment employs Bi-CMOS circuits 50a, 51a, 52a, 50b, 51b, and 52b in place of the write MOS transistors 4a and 4b of the sense amplifier of FIG. 3. This configuration prompts, helped by a large driving capability of the bipolar transistors 50a and 50b, the potentials of common data lines 26a and 26b and the bit lines 25a and 25b to drop to a desired level in a short time so that a write operation can be carried out efficiently.

When the output 27a from the NOR gate becomes "H" at the write operation time and, the transistor 51a turns ON so as to turn the transistor 50a ON; and when the output 27a from the NOR gate becomes "L", the transistor 52a turns ON, so as to cause the base potential of the transistor 50a to be approximately VEE, turning the transistor 50a OFF.

Figure 7:
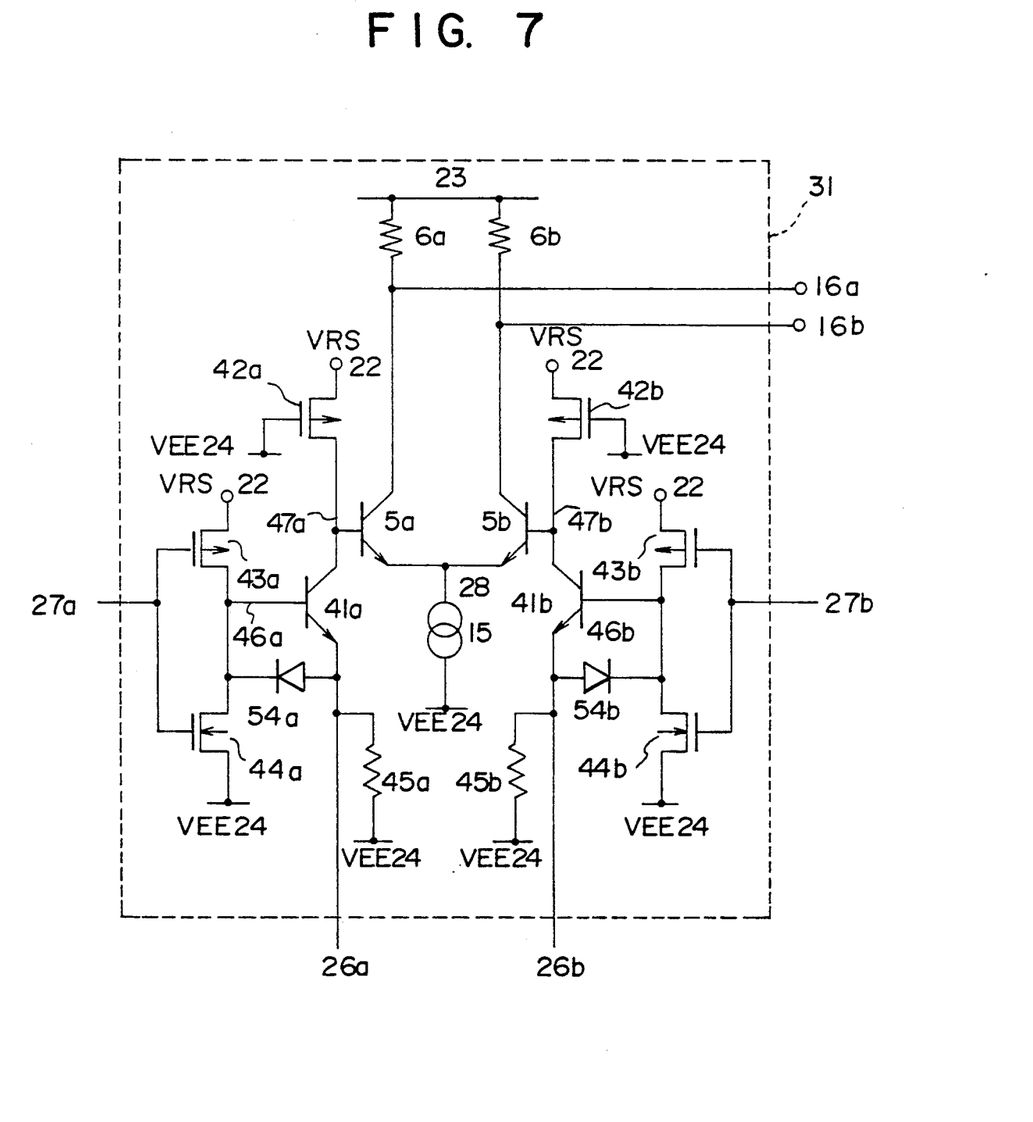
FIG. 7 is a circuit diagram of a main part of the fourth embodiment.

FIG. 7 is a circuit diagram of the main part of the fourth embodiment of the present invention, where diodes 54a and 54b are provided in place of the write MOS transistors 4a and 4b of the embodiment of FIG. 3. The anodes of the diodes 54a and 54b are connected to the common data lines 26a and 26b, while the cathodes thereof are connected to the output nodes 46a and 46b of the C-MOS inverters, namely the bases of the bipolar transistors 41a and 41b. With this configuration, a write current is allowed to flow through the diodes 54a and 54b and the n-channel MOS transistors 44a and 44b. In addition, like the second embodiment, a reverse voltage is prevented from being applied across the emitters and bases of the transistors 41a and 41b. In this embodiment, however, there cannot be a drop of the potential levels of the bases of the transistors 44a and 44b to the potential level of the VEE power supply due to forward voltage drop of the diodes 54a and 54b, thus making it difficult to achieve speed-up.

Figure 8:
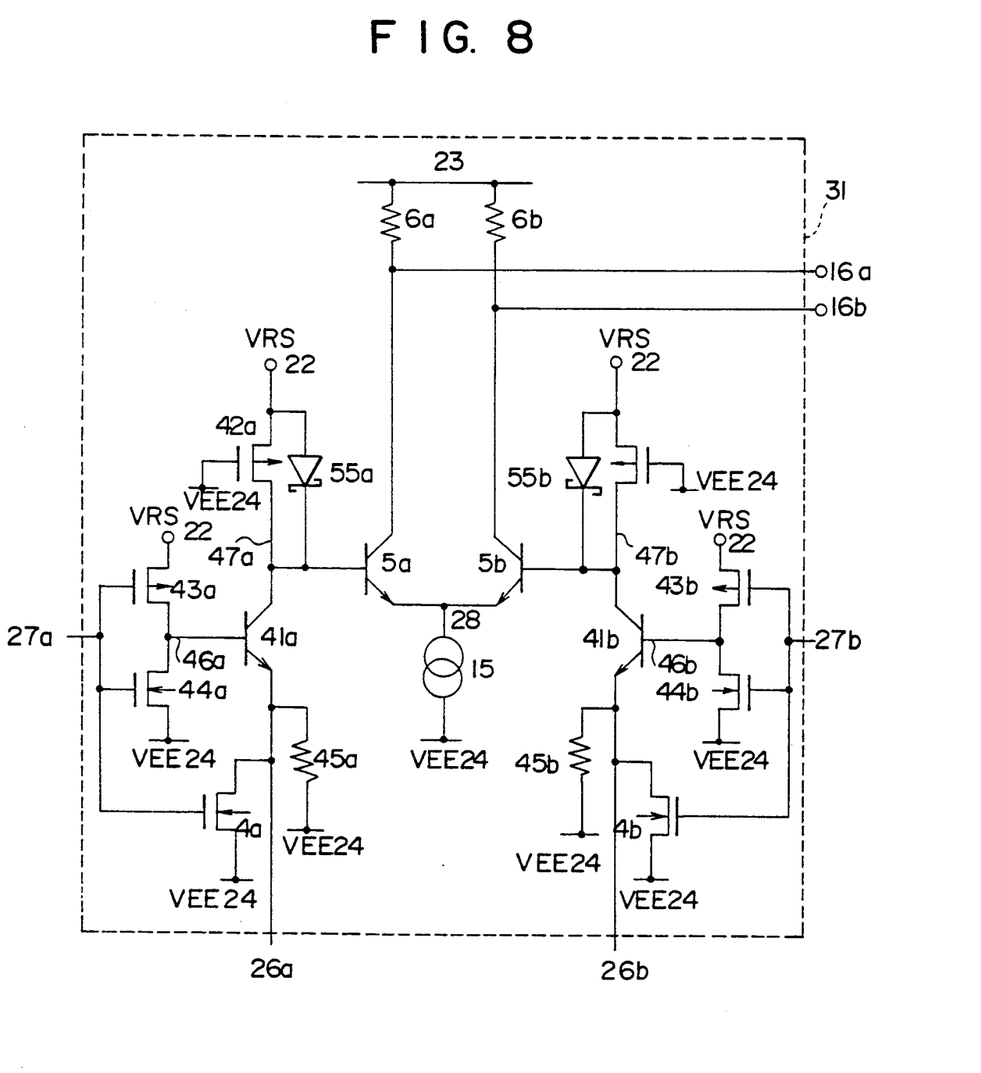
FIG. 8 is a circuit diagram of a main part of the fifth embodiment.

FIG. 8 is a circuit diagram of the main part of the fifth embodiment of the present invention. In this embodiment, Shottky diodes 55a and 55b are provided, the anodes thereof being connected to the VRS power supply, and the cathodes thereof being connected to the collectors of the transistors 41a and 41b. This configuration is designed to eliminate a possibility of saturation of transistors, which is an obstacle to a high speed operation, and which is produced because a transient current, which is generated when, by means of the transistors 41a and 41b, the potential of the common data lines 26a and 26b and the bit lines 25a and 25b are immediately after the write operation, lowers the collector potential of the transistors 41a and 41b, causing the collector potential of the transistors 41a and 41b to be lower than the base potential. Turning the Shottky diodes 55a and 55b ON controls the collector potential of the transistors 41a and 41b to be lower than the VRS by a forward voltage drop (about 0.5 V) of the Shottky diodes 55a and 55b, so that saturation of the transistors 41a and 41b is prevented.

Figure 9:
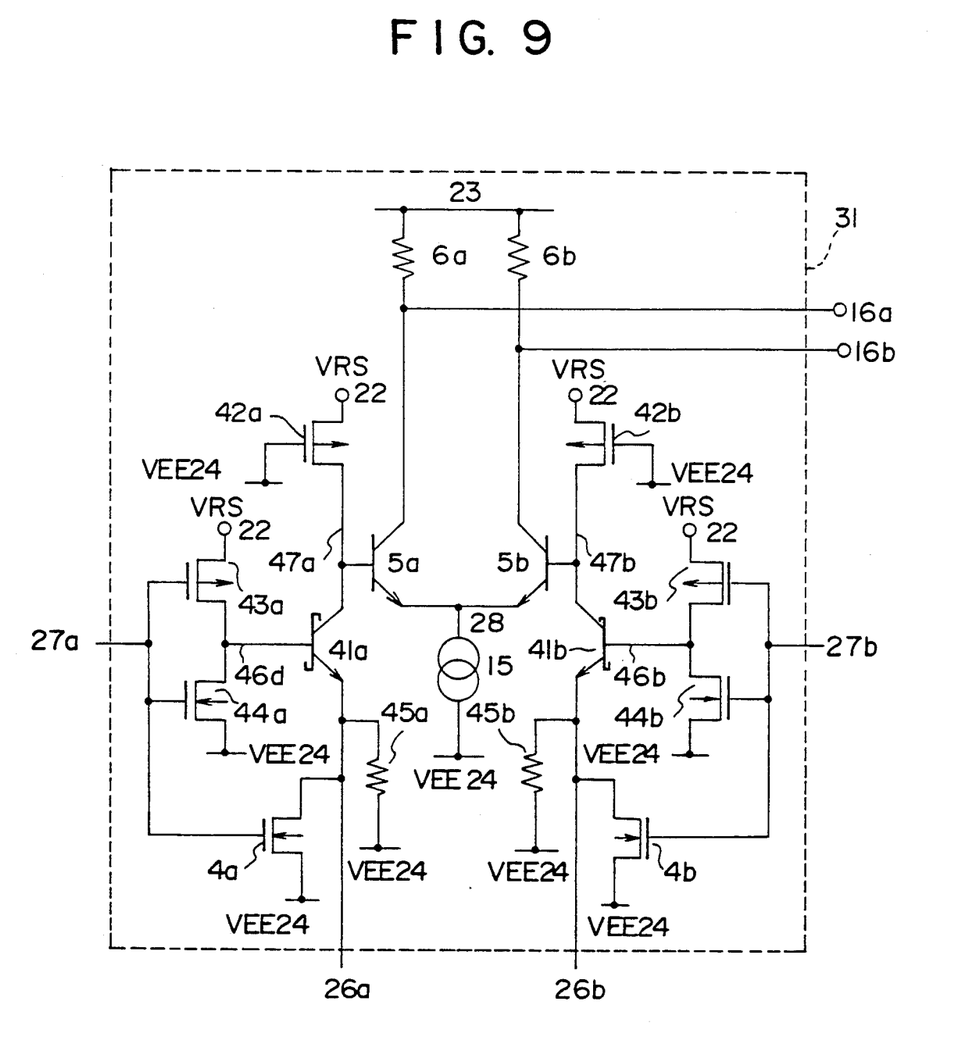
FIG. 9 is a circuit diagram of a main part of the sixth embodiment.

FIG. 9 is a circuit diagram of the main part of the sixth embodiment. This embodiment is configured such that Shottky transistors are used as the transistors 41a and 41b. Shottky transistors are capable of controlling the collector potential to be 0.8 V lower than the base potential, thus preventing a drop of the collector potential during a transient period, and eliminating a possibility of saturation of the transistors 41a and 41b, as in the case of the fifth embodiment.

While the above embodiments assume the use of MOS transistors as the data line load transistors 42a and 42b, resistors can be used in place of the MOS transistors. P-channel MOS transistors can of course be used in place of the load resistors of the differential amplifiers. N-channel or p-channel MOS transistors can be used in place of the resistors 45a and 45b.

POSSIBLE APPLICATION IN INDUSTRY

As has been described, the present invention is effective in that it eliminates a possibility of an excess reverse voltage being applied, at the write operation time, across the emitter and base of transistors constituting a differential amplifier, can prevent a breakdown of these transistors and a degradation of characteristics thereof, and is capable of setting an input level oscillation of a differential amplifier independent of a potential oscillation of bit lines and common data lines so that a potential oscillation of bit lines, etc. can be controlled, irrespective of the precision of detection by a sense amplifier, to be sufficiently small, thereby speeding up the operation of a semiconductor memory.

I claim:

1. A semiconductor memory comprising:
   a plurality of memory cells disposed in rows and at least one column;
   a bit line pair disposed in each column of said memory cells and selectively coupled to each of said memory cells in the column, the memory cell being selected by a row address;
   a pair of write means, each of said write means being coupled to a corresponding one of the bit lines forming said bit line pair, the pair of write means being operable in response to a write signal which instructs a write operation, the pair of write means putting one bit line of said bit line pair to a low potential in response to the write signal, which bit line is put to a low potential depending on the state of said write signal; and
   read means operable in response to a read signal which instructs a read operation, said read means detecting data stored in one of said memory cells via said bit line pair, said read means comprising:
   a pair of bipolar transistors having collectors thereof coupled to a high potential power supply via load means, emitters thereof each coupled to a corresponding one of the bit lines forming said bit line pair, and bases;
   a pair of gate circuits for respectively coupling the bases of said pair of bipolar transistors to the high potential power supply to turn said pair of bipolar transistors ON in response to the read signal during the read operation, and for coupling the base of only one of said pair of bipolar transistors to the high potential power supply in response to the write signal during the write operation, which base is coupled to the high potential power supply depending on the state of the write signal; and
   differential amplifier means having two inputs thereof, each coupled to a collector of a corresponding bipolar transistor of said pair of bipolar transistors, for detecting a potential difference between said inputs.

2. A semiconductor memory as claimed in claim 1, which further comprises:
   high-resistance resistors for coupling the emitters of the pair of bipolar transistors to the low potential.

3. A semiconductor memory as claimed in claim 1, wherein in response to said write signal said pair of gate circuits coupled the base of one of said pair of bipolar transistors to said bit line pair to turn said one bipolar transistor OFF, the base being coupled to said bit line pair being the base not coupled to the high potential power supply.

4. A semiconductor memory as claimed in claim 1, wherein said pair of write means includes MOS transistors.

5. A semiconductor memory as claimed in claim 1, wherein said pair of write means includes bipolar transistors.

6. A semiconductor memory as claimed in claim 1, wherein each write means of said pair of write means includes a diode having an anode thereof coupled to a corresponding bit line of said bit line pair and a cathode thereof coupled to a base of a corresponding bipolar transistor of the pair of bipolar transistors.

7. A semiconductor memory as claimed in claim 1, which further comprises:
   a pair of Schottky diodes coupled in parallel to said load means, the Schottky diodes having anodes thereof coupled to the high potential power supply and cathodes thereof each coupled to a corresponding collector of the pair of bipolar transistors.

8. A semiconductor memory as claimed in claim 1, wherein said pair of bipolar transistors are Schottky transistors.

* * * * *

UNITED STATES PATENT AND TRADEMARK OFFICE
CERTIFICATE OF CORRECTION

PATENT NO. : 5,315,556
DATED : May 24, 1994
INVENTOR(S) : Isao FUKUSHI

It is certified that error appears in the above-indentified patent and that said Letters Patent is hereby corrected as shown below:

Column 6, line 33, after "potential" insert --levels of which outputs reach at approximately the same level as the potential of the VRS power supply 22. The pair of transistors 41a and 41b form an emitter-follower amplifier together with high-resistance resistors 45a and 45b, thus maintaining the data lines 26a and 26b, which are connected to the emitters of the pair of transistors 41a and 41b, at a potential VRS - $V_{BE}$. The collectors of the pair of transistors 41a and 41b are always connected to the VRS power supply 22 via the load transistors 42a and 42b so as to carry a minute amount of current to the VEE power supply via high-resistance resistors 45a and 45b.

UNITED STATES PATENT AND TRADEMARK OFFICE
CERTIFICATE OF CORRECTION

PATENT NO. : 5,315,556
DATED : May 24, 1994
INVENTOR(S) : Isao FUKUSHI

It is certified that error appears in the above-indentified patent and that said Letters Patent is hereby corrected as shown below:

Referring to FIG. 4, assuming that the selected memory cell is 11 and the data stored in this memory cell 11 prompts the driver MOS transistor 13a to be ON, a current will flow from the VRS power supply 22 of the sense amplifier 31 to the VEE power supply 24 via a serial current path consisting of the load transistor 42a, the bipolar transistor 41a, the common data line 26a, the p-channel MOS transistor 8a and the n-channel MOS transistor 9a constituting a column switch, the bit line 25a, the transfer MOS transistor 12a, and the driver MOS transistor 13a. Due to a resistance of the conducting load transistor 42a, there is a significant drop in the potential of the base (node 47a) of the 5a, one of the pair of bipolar transistors.

However, a potential separation is provided by the bipolar transistors 41a and 41b between the bases (nodes 47a

UNITED STATES PATENT AND TRADEMARK OFFICE
CERTIFICATE OF CORRECTION

PATENT NO. : 5,315,556
DATED : May 24, 1994
INVENTOR(S) : Isao FUKUSHI

It is certified that error appears in the above-indentified patent and that said Letters Patent is hereby corrected as shown below:

and 47b) of the pair of bipolar transistors 5a, 5b and the common data lines 26a and 26b. The potential of the common data lines 26a and 26b is maintained at a level lower than the base potential of the bipolar transistors 41a and 41b by $V_{BE}$, that is, at VRS - $V_{BE}$. The lowering of the potential of the above-mentioned node 47a does not affect the potential of the common data line 26a.

At this time, the driver MOS transistor 13b--

Column 10, line 31, "coupled" should be --couples--.

Signed and Sealed this

Seventh Day of February, 1995

Attest:

BRUCE LEHMAN

Attesting Officer        Commissioner of Patents and Trademarks